United States Patent

Sugimura et al.

Patent Number: 5,409,912
Date of Patent: Apr. 25, 1995

[54] LEUSTRODUCSIN H, ITS PREPARATION AND ITS THERAPEUTIC USE

[75] Inventors: Yukio Sugimura; Tomoyuki Shibata; Kazuhiko Tamaki; Shinwa Kurihara; Takafumi Kohama; Akio Shiraishi; Tomowo Kobayashi; Kazuhiko Sasagawa; Naomi Shimazaki, all of Tokyo, Japan

[73] Assignee: Sankyo Company, Limited, Tokyo, Japan

[21] Appl. No.: 224,424

[22] Filed: Apr. 8, 1994

[30] Foreign Application Priority Data

Apr. 23, 1993 [JP] Japan .................................. 5-98058

[51] Int. Cl.$^6$ ..................... A61K 31/665; C07F 9/655
[52] U.S. Cl. ........................................ 514/99; 549/222
[58] Field of Search ........................... 549/222; 514/99

[56] References Cited

U.S. PATENT DOCUMENTS 5,021,406  6/1991  Maeda et al. ........................... 514/99
5,334,587  8/1994  Kohama et al. ....................... 514/99

FOREIGN PATENT DOCUMENTS 0506463  9/1992  European Pat. Off. .

OTHER PUBLICATIONS

Chemical Abstracts, vol. 119, No. 25, 20 Dec. 1993, Columbus, Ohio, US, Abstract No. 269174, Furuhama T. et al, "Manufacture of 2-pyranones with Streptomyces platensis for treatment of thrombocytopenia" of JP-A-93 213 758 (Sankyo Co., Japan), 24 Aug. 1993.

Primary Examiner—Mary C. Lee
Assistant Examiner—Michael G. Ambrose
Attorney, Agent, or Firm—Frishauf, Holtz, Goodman & Woodward

[57] ABSTRACT

A new compound, which we have named Leustroducsin H, has formula (I):

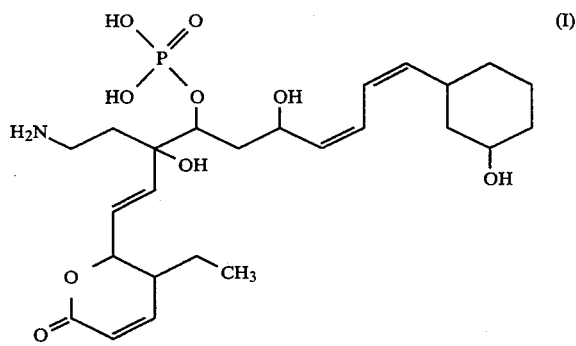

and pharmaceutically acceptable salts thereof. This compound may be prepared by hydrolysis of naturally occurring Leustroducsins and the compound may be used for the treatment or prophylaxis of thrombocytopenia.

4 Claims, No Drawings

LEUSTRODUCSIN H, ITS PREPARATION AND ITS THERAPEUTIC USE

BACKGROUND OF THE INVENTION

The present invention provides a new compound, which we have termed Leustroducsin H, and which has the formula (I) shown hereafter. The invention also provides a method for the preparation of this compound, as well as compositions and methods of therapy using this compound.

The compound of the present invention is a novel compound which stimulates the production of blood platelets and hence is useful in the treatment of thrombocytopenia. Thrombocytopenia may be induced by various causes, such as immune abnormality or adverse reactions after cancer chemotherapy or radiotherapy. It is a severe disease which, if aggravated, causes bleeding throughout the body and sometimes results in death. At present, the only sure way to treat thrombocytopenia is by symptomatic therapy involving blood platelet transfusion.

Various types of cytokine are known, which compounds have a hematopoietic activity. These include certain interleukins, for example interleukin 6 (hereinafter abbreviated to IL-6), interleukin 11 (hereinafter abbreviated to IL-11) and leukemia inhibitory factor (hereinafter abbreviated to LIF). Amongst other activities, these compounds are known to stimulate the production of blood platelets and, as such, are expected to be clinically useful [Ishibashi et al., Blood 74, 1241–1244 (1989); Asano et al., Blood 75, 1602–1605 (1990); Okada et al., Blood Tumor 22, 23–31 (1991)].

It has been found that the administration of these compounds themselves to humans by various routes results in clear pharmacological effects, which leads to the possible use of these compounds in therapy. However, it is thought that these compounds are essentially produced in vivo by certain kinds of cell (e.g. lymphocytes, monocytes, fibroblasts, vascular endothelial cells and stromal cells) through a complicated regulatory system, and that they play homeostatic roles in the production of various kinds of blood cell. Accordingly, if these compounds are administered without any consideration for the delicate balance of this regulatory mechanism, several side effects may be observed, which may be caused by the imbalance of this regulatory mechanism; examples of such side effects include hepatic tissue damage, weight loss, fever and rigor.

It is also known that various kinds of low-molecular weight immunoactivators, such as muramyldipeptides (hereinafter abbreviated to MDP) are capable of increasing the total number of blood platelets [R. Nakajima et al., Arzneimittel-Forsch./Drug Research 41, 60–65 (1989)]. It is thought that these compounds stimulate production of IL-6 indirectly via the activation of monocytes and macrophages. The IL-6 produced then causes an increase in the number of thrombocytes. However, it is also known that other, perhaps less desirable, physiological effects based on the activation of macrophages, for example, formation of monokines, such as interleukin 1 (IL-1) and tumor necrosis factor (TNF), occur at the same time. Adverse reactions, such as fewer, are also observed [Jap. J. Radiotherapy 48 (4), 514 (1988)].

It is apparent, therefore, that there remains a need for an agent which is capable of stimulating blood platelet formation and which can therefore be used in the treatment of thrombocytopenia, but which agent does not cause an imbalance in any internal regulatory mechanism or result in adverse effects, such as those described above.

European Patent Publication No. 506,463 discloses certain new pyranone derivatives, named as Leustroducsin A, B and C, which have the following formula:

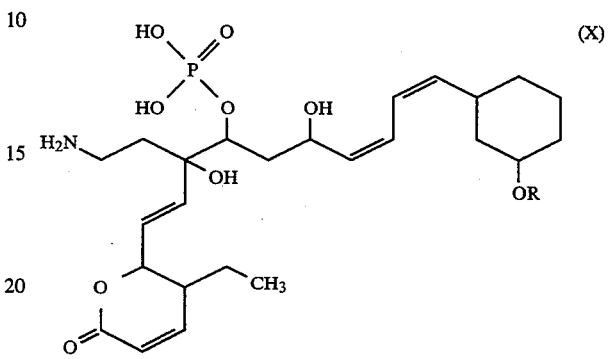

in which R represents a 5-methylhexanoyl group, a 6-methyloctanoyl group or a 7-methyloctanoyl group respectively. These compounds, which were isolated from a strain of the micro-organism Streptomyces platensis, are disclosed to have activity in: reduction of adverse reactions resulting from cancer chemotherapy or radiotherapy, protection against infections, activation of macrophages, improvement of cerebral function as well as activity as antifuneral agents.

Japanese Patent Publication No. Hei 5-213758, which was published on 24th Aug. 1993, describes the use of Leustroducins A, B and C in the treatment of thrombocytopoiesis.

European Patent Publication No. 329 361 discloses certain new 2-pyranone derivatives which resemble the compound of the present invention, except that they are substituted in a manner similar to the substitution in the compounds of European Patent Publication No. 506 463, above. These prior art compounds are, furthermore, only said to be agricultural biocides and are not shown in the published art to have the valuable and unexpected therapeutic and prophylactic activities of the compound of the present invention.

Further compounds, very similar to those described in European Patent Publication No. 329 361 and having essentially the same utility, are described in Japanese Patent Application Kokai Hei 2-186.

The Journal of Antibiotics, 42 (1989) 1331–1343 discloses a novel antitumor compound, which the authors call "Phospholine" and which is produced by a micro-organism of the genus Streptomyces. This compound, like that of the present invention, has both an amino group and a phosphoric acid group, but has a different molecular formula. The compound is, therefore, clearly distinguished from that of the present invention.

BRIEF SUMMARY OF THE INVENTION

It is therefore an object of the present invention to provide a new leustroducsin having a valuable pharmacological activity.

In particular, it is believed that the compound of the invention has great potential in the treatment of thrombocytopenia, particularly when induced by cancer chemotherapy or radiotherapy and immune abnormalities.

Thus, the present invention provides a compound of formula (I):

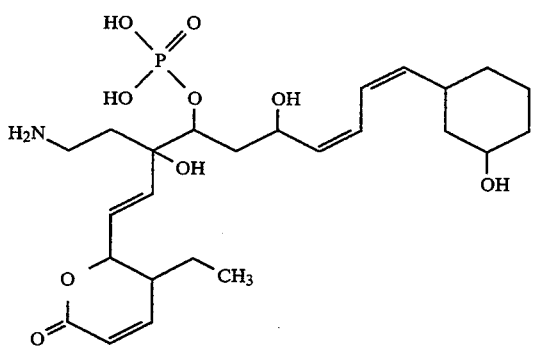

and pharmaceutically acceptable salts thereof. This compound has been named by us as Leustroducsin H.

The invention also provides a process for the preparation of Leustroducsin H, which will be described in more detail hereinafter.

The invention also provides a pharmaceutical composition comprising Leustroducsin H or a pharmaceutically acceptable salt thereof, in admixture with a pharmaceutically acceptable diluent or carrier.

The invention still further provides a method for the treatment or prophylaxis of thrombocytopenia, particularly resulting from the treatment of cancer by chemotherapy or radiotherapy, which method comprises administering an effective amount of Leustroducsin H or a pharmaceutically effective salt thereof to a mammal, which may be human, suffering from, or susceptible to thrombocytopenia.

DETAILED DESCRIPTION OF THE INVENTION

It is clear from the above formula that the leustroducsin of the present invention contains a number of asymetric carbon atoms and several double bonds. It can therefore form various optical and geometric isomers. Although these are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

The leustroducsin of the present invention contains both an acidic group (the phosphoric acid group) and a basic group (the amino group) and can thus form salts. There is no particular restriction on the nature of these salts, provided that, where they are intended for therapeutic use, they are pharmaceutically acceptable. Where they are intended for non-therapeutic uses, e.g. as intermediates in the preparation of other, and possibly more active, compounds, even this restriction does not apply. The compounds of the present invention can form salts with bases. Examples of such salts include: salts with an alkali metal, such as sodium, potassium or lithium; salts with an alkaline earth metal, such as barium or calcium; salts with another metal, such as magnesium or aluminum; organic base salts, such as a salt with dicyclohexylamine; and salts with a basic amino acid, such as lysine or arginine. The compounds of the present invention can also form acid addition salts. Examples of such acid addition salts include: salts with mineral acids, especially hydrohalic acids (such as hydrobromic acid, hydroiodic acid or hydrochloric acid), nitric acid, perchloric acid, carbonic acid, sulfuric acid or phosphoric acid; salts with lower alkylsulfonic acids, such as methanesulfonic acid, trifluoromethane- sulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid or citric acid; and salts with amino acids, such as glutamic acid or aspartic acid.

The leustroducsin of the present invention may be prepared by the hydrolysis of a compound of formula (II) or of a salt thereof:

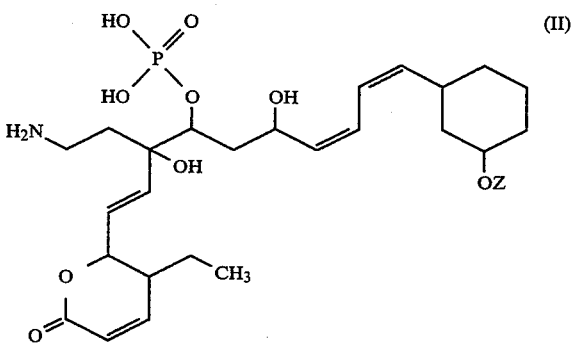

in which Z represents an acyl group, followed, optionally, by salifying the compound obtained.

The hydrolysis reaction may be effected using any hydrolysis agent generally used for reactions of this type such as, for example, a hydrolytic enzyme or a base.

In formula (II), above, Z represents an acyl group. The precise nature of the acyl group is not essential to the present invention, so long as this can be removed by hydrolysis to afford the compound of formula (I). We have generally found that compounds in which Z represents a straight or branched chain aliphatic acyl group, or a cyclic aliphatic acyl group, having from 2 to 16 carbon atoms, are suitable starting materials. When Z represents such an acyl group this may be, for example, a butyryl, isobutyryl, isovaleryl, 2-methylbutyryl, 4-methylvaleryl, cyclohexanecarbonyl, 4-methylhexanoyl, 5-methylhexanoyl, 6-methylheptanoyl, cyclohexylethylcarbonyl, octanoyl, 6-methyloctanoyl or 7-methyloctanoyl group.

Compounds of formula (II), for use as starting materials in the process of the present invention, in which Z represents an isobutyryl, isovaleryl, 4-methylvaleryl, cyclohexanecarbonyl or 4-methylhexanoyl group are known and described in, for example, Journal of Antibiotics 42, 1019–1036 (1989).

Compounds of formula (II), for use as starting materials in the process of the present invention, in which Z represents a butyryl, isobutyryl, isovaleryl, 2-methylbutyryl, cyclohexanecarbonyl, 4-methylhexanoyl, 6-methylheptanoyl, cyclohexylethylcarbonyl or octanoyl group are known and disclosed in, for example, European Patent Publication No. 329 361. Starting materials in which Z is one of these groups may be prepared by the culture of the micro-organism strain *Streptomyces platensis* SAM 0654 and separation of the desired compound from the culture liquid. *Streptomyces platensis*

SAM 0654 was deposited as number FERM BP-1668 in connection with European Patent Publication No. 329 361 at the Fermentation Research Institute, Agency of Industrial Science and Technology on 22nd Jan. 1988. Suitable techniques for culture of the micro-organism and separation of the desired compound are given in European Patent Publication No. 329 361.

Those compounds of formula (II) in which Z represents a 5-methylhexanoyl, 6-methyloctanoyl or 7-methyloctanoyl group are also known and described in, for example, European Patent Publication No. 506 463.

Compounds of formula (II), for use as starting materials in the process of the present invention in which Z represents a 4-methylhexanoyl, 5-methylhexanoyl, 6-methylheptanoyl, cyclohexylethylcarbonyl, octanoyl, 6-methyloctanoyl or 7-methyloctanoyl group are known and maybe prepared, for example, by culture of *Streptomyces platensis* SANK 60191 followed by separation from the culture liquid. Suitable conditions for the culture of this micro-organism are given in, for example, European Patent Publication No. 506 463. *Streptomyces platensis* SANK 60191 was deposited under number FERM BP-3288 at the Fermentation Research Institute, Agency of Industrial Science and Technology, on 20th Feb. 1991 in connection with European Patent Publication No. 506 463.

Method 1: Use of a Hydrolytic Enzyme

In this method, a compound of formula (I) is prepared by reaction of a compound of formula (II) with a hydrolytic enzyme.

The precise nature of the enzyme is not critical to the present invention and any hydrolytic enzyme which is commonly used for reactions of this type may equally be used here. We generally prefer to use enzymes such as porcine liver esterase (PLE), lipase, acetylesterase, Takadiastase or cholesterol esterase.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: a mixture of an alcohol, such as methanol or ethanol, with a buffer solution, preferably a phosphate buffer solution, having a pH of from about 6 to 8, or a mixture of a ketone, such as acetone or methyl ethyl ketone, with a buffer solution, preferably a phosphate buffer solution, having a pH of from about 6 to 8.

We particularly prefer to perform this reaction using either PLE or lipase as the hydrolytic enzyme in a solvent comprising a mixture of a phosphate buffer of pH 6 to 8 with acetone or methanol.

The reaction can take place over a wide range of temperatures, and the precise reaction temperature is not critical to the invention, although the preferred temperature may vary, depending upon the nature of the starting compound and the enzyme used, as well as the nature of the solvent. In general, we find it convenient to carry out the reaction at a temperature of from about 10° C. to 40° C., preferably from about 20° C. to 40° C.

The time required for the reaction may also vary widely, depending on many factors, notably the reaction temperature and the nature of the starting compound, the enzyme and the solvent: employed. However, provided that the reaction is effected under the preferred conditions outlined above, a period of from 12 hours to 30 days, preferably 3 days to 15 days, will usually suffice.

After completion of the reaction, the compound of formula (I) may be extracted from the reaction mixture and purified using conventional means. One example of a suitable technique includes removal of the water-miscible solvent, such as acetone, by distillation under reduced pressure, followed by extraction of the resulting aqueous layer using an organic solvent, such as ethyl acetate. This may then be further followed by fractionation and purification of the aqueous layer, for example using a Cosmosil (a registered trademark) open column.

Method 2: Use of a Base

In this method, the compound of formula (I) is obtained by reaction of a compound of formula (II) with a base.

There is no particular restriction on the nature of the base employed, and any base commonly used in reactions of this type may equally be used here, provided that it has no adverse effect on any part of the molecule or the reagents. Examples of preferred bases include: an inorganic base, for example, an alkali metal carbonate such as sodium carbonate, potassium carbonate, cerium carbonate or lithium carbonate; an alkali metal hydrogencarbonate such as sodium hydrogencarbonate, potassium hydrogencarbonate or lithium hydrogencarbonate; an alkali metal hydroxide such as sodium hydroxide, potassium hydroxide or lithium hydroxide; or an alkaline earth metal hydroxide such as barium hydroxide, magnesium hydroxide or calcium hydroxide. Of these, we prefer to use an alkali metal carbonate or an alkali metal hydrogencarbonate, most preferably sodium carbonate, potassium carbonate or sodium hydrogencarbonate.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: a mixture of an alcohol, such as methanol or ethanol, with water; or a mixture of a ketone, such as acetone or methyl ethyl ketone, with water.

The reaction can take place over a wide range of temperatures, and the precise reaction temperature is not critical to the invention, although the preferred temperature may vary, depending upon the nature of the starting compound and the base as well as the nature of the solvent. In general, we find it convenient to carry out the reaction at a temperature of from about 0° C. to 40° C., preferably from about 5° C. to 30° C.

The time required for the reaction may also vary widely, depending on many factors, notably the reaction temperature and the nature of the starting compound, the base and the solvent employed. However, provided that the reaction is effected under the preferred conditions outlined above, a period of from 3 hours to 5 days, preferably 3 hours to 2 days, will usually suffice.

After completion of the reaction, the compound of formula (I) may be extracted from the reaction mixture and purified using conventional means. One example of a suitable technique includes removal of the water-miscible solvent, such as acetone, by distillation under reduced pressure, followed by extraction of the resulting aqueous layer using an organic solvent, such as ethyl acetate. This may then be further followed by fractionation and purification of the aqueous layer, for example using a Cosmosil (a registered trademark) open column.

BIOLOGICAL ACTIVITY

The following assay demonstrates the activity of the compound of the present invention as a thrombopoietic agent. We use "thrombopoietic agent" in the present invention to mean an agent which, after administration to the body, induces blood platelet production in vivo, as well an agent which may be used in the therapy of thrombocytopenia induced by various causes, such as immune abnormality and adverse reactions after cancer chemotherapy or radiotherapy.

EXPERIMENT 1

Enhancement of Thrombocytopoiesis in Mice after Intravenous Administration of Leustroducsin H The thrombopoietic activity of the compound of the present invention may be assayed using the method of Ishibashi et. al., reported in Blood 74, 1241–1244 (1989).

In more detail, the compound of the present invention to be tested was dissolved in a physiological saline solution containing 1.25% v/v of aqueous ethanol. A sample of this mixture was intravenously administered to C57BL mice (female, each 7 weeks old) at 24 hour intervals over a test period of 5 days. Control mice were given only a physiological saline solution containing 1.25% v/v aqueous ethanol. 72 hours after the final administration, blood samples were taken from the orbit of the animals eye and the number of blood platelets in the samples was counted. The assay was conducted by the electric resistance method using an automatic blood cell counter (K-1000, Toa-Iyo Denshi Co.). The results are shown in Table 1:

TABLE 1

| Compound | Dose (mg/kg) | Test Period | Platelet count ($\times 10^4/\mu L$) |
| --- | --- | --- | --- |
| Control | 0 | 5 | 93.31 ± 6.34* |
| Leustroducsin H | 0.05 | 5 | 130.08 ± 1.67 |
| | 0.1 | 5 | 125.71 ± 6.60 |
| | 0.5 | 5 | 121.18 ± 9.22 |
| | 1 | 5 | 127.70 ± 3.34 |

* = mean ± SE.

The precise reaction conditions outlined above are not essential to the determination of the blood platelet count and variations, for example in the animal used for testing, the mode of administration and the overall time period and periods of adminstration, may be included. Thus, for example, the test animal may be a mouse, rat, dog or monkey and/or the compound to be tested may be adminstered parenterally, intraperitoneally, intramuscularly or by subcutaneous injection.

EXPERIMENT 2

Toxicity Study 4 mg/kg of Leustroducsin H was intravenously administered to BALB/c mice. No deaths were observed after 10 days.

It is apparent from the above results that Leustroducsin H of the present invention demonstrates excellent thrombopoietic activity in vivo and low toxicity and, as such, is useful as a therapeutic agent in the treatment of thrombocytopenia induced by various causes, particularly by immune abnormality or adverse reactions after cancer chemotherapy or radiotherapy.

For this purpose, the compounds of formula (I) can be administered orally in the form of tablets, capsules, granules, powders or syrups, or parenterally by intravenous, subcutaneous or intramuscular injection, suppositories or the like. These pharmaceutical formulations can be prepared by mixing the compounds of the present invention with one or more adjuvants, such as excipients (e.g. organic excipients including sugar derivatives, such as lactose, sucrose, glucose, mannitol or sorbitol; starch derivatives, such as corn starch, mashed potato, $\alpha$-starch, dextrin or carboxymethyl starch; cellulose derivatives, such as crystalline cellulose, low hydroxypropyl-substituted cellulose, hydroxypropylmethyl cellulose, carboxymethyl cellulose, carboxymethyl cellulose calcium or internally bridged carboxymethyl cellulose sodium; gum arabic; dextran; and Pullulan; inorganic excipients including silicates, such as light silicic acid anhydride, synthetic aluminum silicate or magnesium metaosilicic acid aluminate; phosphates, such as calcium phosphate; carbonates, such as calcium carbonate; and sulfates, such as calcium sulfate); lubricants (e.g. metal stearates, such as stearic acid, calcium stearate or magnesium stearate; talc; colloidal silica; waxes, such as beeswax or spermaceti; boric acid; adipic acid; sulfates, such as sodium sulfate; glycol; fumaric acid; sodium benzoate; DL-leucine; sodium salts of aliphatic acids; lauryl sulfates, such as sodium laurylsulfate or magnesium laurylsulfate; silicates, such as silicic acid anhydride or silicic acid hydrate; and the foregoing starch. derivatives); binders (e.g. polyvinyl pyridone, Macrogol; and similar compounds to the excipients described above); disintegrating agents (e.g. similar compounds to the excipients described above; and chemically modified starch-celluloses, such as Cross-carmelose sodium, sodium carboxymethyl starch or bridged polyvinyl pyrrolidone); stabilizers (e.g. p-hydroxybenzoates, such as methylparaben or propylparaben; alcohols, such as chlorobutanol, benzyl alcohol or phenylethyl alcohol; benzalkonium chloride; phenols, such as phenol or cresol; thimerosal; dehydroacetic acid; and sorbic acid); corrigents (e.g. sweeteners, vinegar or perfumes, such as those conventionally used); diluents and the like.

The dose varies depending upon the condition and age of the patient and upon the route and type of administration but, for example, the compounds of the present invention can be administered in a daily dose of from 0.01 to 10 mg/kg (preferably 0.01 to 1 mg/kg) either as a single dose or as divided doses.

The preparation of certain of the compounds of the invention is further illustrated by the following Examples. The subsequent Preparations illustrate the preparation of certain of the starting materials used in these Examples.

EXAMPLE 1

5.61 g of the crude oily substance obtained in Step B of Preparation 1, below, were dissolved in 130 ml of acetone. 1400 ml of 0.05M phosphate buffer solution ($NaH_2PO_4/Na_2HPO_4$, pH=6.7) were then added and the resulting mixture was stirred. 807 mg of porcine liver esterase (PLE, Product of Amano Pharm. Co., Ltd.) were then added to the mixture and the mixture was stirred at 35° C. The starting material has a retention time of 8.8 minutes on high performance liquid chromatography, and the progress of the reaction was therefore monitored using this technique. PLE was added in amounts of 0.82 g, 1.52 g, 1.02 g and 0.9 g to the mixture over a period of two weeks at 35° C., and the resulting mixture was stirred for two weeks. At the end of this time, the reaction solution was filtered using a Celite (a registered trademark) filter aid to remove the PLE. The filtrate was then extracted with ethyl acetate and the aqueous layer was fractionated and purified by column chromatography through 400 g of Cosmosil 75C18-OPN, (a registered trademark for a product of Nakaraitesque Inc.), using aqueous methanol as the eluent, to obtain 1.73 g of Leustroducsin H.

High performance liquid chromatography was carried out under the following conditions:

Column: Cosmosil 5C18-AR ™ 4.6×250 mm; (Product of Nakaraitesque Inc.)

Eluting solvent.: 20% v/v acetonitrile: 0.5% v/v triethylamine: 79.5% v/v phosphate buffer (pH 3.0);
Flow rate: 1.0 ml/min;
Wave length: 230 nm.

Fast Atom Bombardment Mass Spectrum:
m/z=530 (m+1), 528 (m−1)

Nuclear Magnetic Resonance Spectrum (270 MHz, $D_2O$) δ ppm:
7.02 (1H, doublet of doublets, J=5.4 & 9.8 Hz);
6.21 (1H, doublet of doublets, J=11.7 & 20.5 Hz);
6.12 (1H, doublet of doublets, J=12.2 & 20.5 Hz);
5.93-5.84 (2H, multiplet);
5.71 (1H, doublet, J=16.6 Hz);
5.32-5.25 (2H, multiplet);
3.94 (1H, doublet of triplets, J=3.4 & 10.3 Hz);
3.48 (1H, multipier);
2.93 (2H, triplet, J=7.8 Hz);
2.53-2.40 (2H, multipier);
2.03 (1H, multipier);
1.80-0.73 (13H, multiplet);
0.73 (3H, triplet, J=7.8 Hz).

EXAMPLE 2

20 mg of a compound of formula (II), above, in which Z represents a 4-methylhexanoyl group [prepared as described in Step B of Preparation 1, below], were dissolved in a small amount of methanol. The resulting solution was diluted with phosphate buffer (pH 6.7), after which 10 mg of PLE (a product of Amano Pharm. Co., Ltd.) were added and the mixture was stirred for 6 days at 30° C. At the end of this time, the reaction solution was filtered. Any methanol remaining was removed from the filtrate by distillation under reduced pressure, and the resulting aqueous solution was fractionated and purified through a C18-Cosmosil column using aqueous methanol as the eluent. The fraction which eluted with 20% by volume aqueous methanol afforded 13 mg of a compound showing the same physical properties as those of the compound obtained in Example 1, above.

EXAMPLE 3

A procedure similar to that described in Example 2, above, was followed, but using 50 mg of a compound of formula (II), above, in which Z represents a 5-methylhexanoyl group [prepared as described in Step B of Preparation 1, below], to obtain 30 mg of Leustroducsin H.

Following a procedure similar to that described in Example 2, above, Leustroducsin H, having the properties described in Example 1, above, was also prepared from a compound of formula (II) in which Z represents the following groups. The amounts of the starting material and of the compound of the present invention obtained are shown below.

TABLE 2

| Example No. | Z | Amount of starting compound | Yield |
|---|---|---|---|
| 4 | Isobutyryl | 20 mg | 14 mg |
| 5 | Isovaleryl | 20 mg | 14 mg |
| 6 | 2-Methylbutyryl | 20 mg | 10 mg |
| 7 | Cyclohexanecarbonyl | 20 mg | 8 mg |

EXAMPLE 8

20 mg of a compound of formula (II) in which Z represents a 6-methylheptanoyl group [prepared as described in Step B of Preparation 1, below] were dissolved in a small amount of aqueous methanol. A saturated aqueous solution of sodium hydrogencarbonate was then added to the mixture, and the resulting solution was stirred for one day. At the end of this time, the pH of the reaction solution was adjusted to pH 2 by the addition of an appropriate amount of aqueous hydrochloric acid and the resulting mixture was fractionated and purified through a Cosmosil C18-column, to provide 3 mg of Leustroducsin H.

PREPARATION 1

Culture and Isolation of the Starting Compounds

1 (A) Culture

One platinum loopful of spores of *Streptomyces platensis* SANK 60191 (FERM BP-3288) was inoculated into a 500 ml Erlenmeyer flask fitted with baffle plates and containing 100 ml of a previously sterilized culture medium (having the composition described below), and the microorganism was cultured for 3 days at 28° C. and at 200 rpm (a rotation radius of 7 cm), using a rotary shaker.

| Culture Medium: | |
|---|---|
| Soluble starch | 30 g |
| Raw yeast | 10 g |
| Soy bean powder | 7 g |
| Fish meal | 5 g |
| Corn steep liquor | 2 g |
| Meat extract | 1 g |
| Calcium carbonate | 1 g |
| Water to | 1000 ml |
| | pH 7 (before sterilization). |

15 liters of the same culture medium as was used for the seed culture was charged into each of four 30 liter stainless jal fermenters, and was sterilized by heating it at 120° C. for 30 minutes. 150 ml of the seed culture liquid prepared as described above were then added. The mixture was cultivated for 3 days at 28° C. with aeration at an air flow rate of 15 liters/minute, whilst stirring. In order for the oxygen concentration in the liquid to be maintained at 5 ppm, the stirring rate was automatically controlled within the range from 100 to 300 rpm.

1 (B) Isolation 2.4 kg of Celite 545 (a trade name for a product of Johns & Manville Project Corporation, USA) were added as a filter aid to 60 liters of the culture liquid obtained as described in 1(A) above, and the mixture was filtered. After filtration of the culture liquid, 7.2 kg of bacterial cells were obtained. The cells were extracted once with 30 liters of 50% v/v aqueous acetone, and twice with 20 liters of 80% v/v aqueous acetone each time. These extracts were combined and the organic solvent was distilled off using a rotary evaporator. Sufficient aqueous hydrochloric acid was added to the residue to adjust its pH to a value of 2.0, and then the mixture was extracted twice, each time with 10 liters of ethyl acetate. The extracts were combined, and 10 liters of a 1% w/v aqueous solution of sodium hydrogencarbonate were added to the combined extracts. The active fractions were transferred into the aqueous layer and the ethyl acetate layer was removed. This ethyl acetate layer was again extracted with 5 liters of a 1% w/v aqueous solution of sodium hydrogencarbonate. The sodium hydrogencarbonate solutions were combined and the pH of the combined solution was adjusted to a value of 2.0 by the addition of aqueous hydrochloric acid. The solution was extracted twice, each time with 10 liters of ethyl acetate. The organic extracts were combined, washed with water and then with a saturated aqueous solution of sodium chloride, and then dried over anhydrous sodium sulfate. During continuous addition of methanol, the solution was then condensed by evaporation under reduced pressure, using a rotary evaporator, to obtain 10 ml of an oily substance. This oily substance was dissolved in 100 ml of 60% v/v aqueous methanol, and the resulting solution was adsorbed on Sep-Pak Vac 20 cc $C_{18}$ Cartridges (a trade name for a product of Waters Co., USA). Impurities were eluted with 30 ml of 60% v/v aqueous methanol. The leustroducsins were then eluted with 15 ml of 100% methanol, and the eluate was condensed to obtain 800 mg of an oily substance. This oily substance was used directly, and without further purification, in Example 1, above. In order to purify the material, this oily substance was dissolved in 10 ml of methanol, and subjected to high performance liquid chromatography. The fractions showing peaks near 13 minutes, 19 minutes and 24 minutes were collected and are referred to as "Raw Fraction A", "Raw Fraction B" and "Raw Fraction C", respectively. The conditions used for the chromatography are shown below.

Preparative liquid chromatography
  Column: Radial-Pak 25×10 (Waters, USA)
  Eluting solvent: 50% by volume aqueous acetonitrile, containing 0.5% triethylamine - phosphate buffer, pH 3.0
  Flow rate: 9 ml/min.
  Wave length: 230 nm After condensation of all of these peaks, the resulting fractions were subjected to preparative high performance liquid chromatography. Raw Fraction A was subjected to preparative chromatography to collect the peaks near 53 and 56 minutes under the following conditions; it was then desalted and condensed using Sep-Pak to obtain 22.03 mg of a compound of formula (II) in which Z represents a 4-methylhexanoyl group and 11.66 mg of Leustroducsin A.

Preparative conditions for Raw Fraction A
  Column: Cosmosil 5C 18-AR 20×250 mm (Nakaraitesque Inc.)
  Eluting solvent: 42% v/v aqueous acetonitrile, containing 0.5% triethylamine - phosphate buffer, pH 3.0
  Flow rate: 9 ml/min.
  Wave length: 230 nm.

Raw Fraction B was subjected to preparative chromatography to collect the peaks near 74 minutes, 79 minutes and 82 minutes under the following conditions; it was then desalted and condensed using Sep-Pak to obtain 26.16 mg of a compound of formula (II) in which Z represents a 6-methylheptanoyl group, 23.24 mg of a compound of formula (II) in which Z represents a cyclohexylethylcarbonyl group and 3.24 mg of a compound of formula (II) in which Z represents an octahoyl group.

Preparative conditions for Raw Fraction B
  Column: Cosmosil 5C 18-AR 20×250 mm (Nakaraitesque Inc.)
  Eluting solvent: 47% v/v aqueous acetonitrile, containing 0.5% triethylamine - phosphate buffer, pH 3.0
  Flow rate: 9 ml/min.
  Wave length: 230 nm.

Raw Fraction C was subjected to preparative chromatography to collect the peaks near 47 minutes and 51 minutes, under the following conditions; it was then desalted and condensed by Sep-Pak to obtain 9.83 mg of Leustroducsin B and 5.22 mg of Leustroducsin C.

Preparative conditions for Raw Fraction B
  Column: Cosmosil 5C 18-AR 20×250 mm (Nakaraitesque Inc.)
  Eluting solvent: 47% v/v aqueous acetonitrile, containing 0.5% triethylamine - phosphate buffer, pH 3.0
  Flow rate: 9 ml/min.
  Wave length: 230 run.

PREPARATION 2

Culture and isolation of the starting compounds

*Streptomyces platensis* SAM-0654 (FERM BP-1668) was cultured and compounds of formula (II) in which Z represents each of a butyryl, isobutyryl, isovaleryl, 2-methylbutyryl, cyclohexanecarbonyl, 4-methylhexanoyl, 6-methylheptanoyl, cyclohexylethylcarbonyl and octanoyl group were isolated from the culture broth, according to the methods described in European Patent Publication No. 329 361.

| Capsule preparation | |
| --- | --- |
| Leustroducsin H | 100 mg |
| Lactose | 100 mg |
| Corn starch | 148.8 mg |
| Magnesium stearate | 1.2 mg |
| Total | 350 mg |

The above ingredients were mixed, the resulting powder was passed through a 20-mesh sieve (Tyler standard) and then filled into capsules.

We claim:

1. A compound of formula (I):

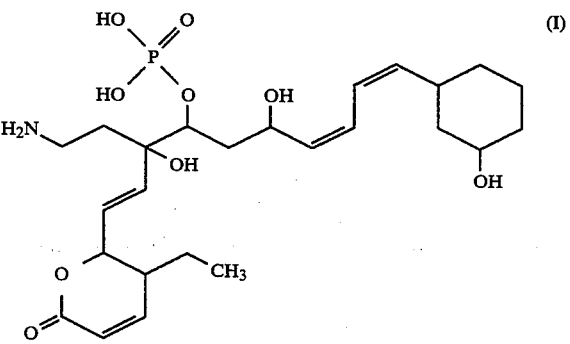

and pharmaceutically acceptable salts thereof.

2. A pharmaceutical composition comprising the compound of formula (I) or a pharmaceutically acceptable salt thereof, as claimed in claim 1, in admixture with a pharmaceutically acceptable diluent or carrier.

3. A method for the treatment or prophylaxis of thrombocytopenia, which method comprises administering an effective amount of the compound of formula (I) or a pharmaceutically acceptable salt thereof, as claimed in claim 1, to a mammal, suffering from or susceptible to thrombocytopenia.

4. The method of claim 3, wherein the mammal is a human.

* * * * *